US010339789B1

(12) United States Patent
MacDonald

(10) Patent No.: US 10,339,789 B1
(45) Date of Patent: Jul. 2, 2019

(54) NURSE CALL PILLOW SPEAKER WITH BROWNOUT PROTECTION

(71) Applicant: Curbell Medical Products, Inc., Orchard Park, NY (US)

(72) Inventor: Daniel J. MacDonald, East Amherst, NY (US)

(73) Assignee: Curbell Medical Products, Inc., Orchard Park, NY (US)

( * ) Notice: Subject to any disclaimer, the term of this patent is extended or adjusted under 35 U.S.C. 154(b) by 6 days.

(21) Appl. No.: 16/038,468

(22) Filed: Jul. 18, 2018

(51) Int. Cl.
*A47G 9/10* (2006.01)
*A61B 5/00* (2006.01)
*G08B 5/22* (2006.01)
*G08B 25/00* (2006.01)
*G08B 25/01* (2006.01)
*G08B 25/10* (2006.01)
*G16H 40/20* (2018.01)

(52) U.S. Cl.
CPC ......... *G08B 25/016* (2013.01); *A47G 9/1045* (2013.01); *G08B 5/223* (2013.01); *G08B 25/009* (2013.01); *G08B 25/014* (2013.01); *A61B 5/746* (2013.01); *G08B 25/10* (2013.01); *G16H 40/20* (2018.01)

(58) Field of Classification Search
CPC .... G08B 25/016; G08B 5/223; G08B 25/009; G08B 25/014; G08B 25/10; A47G 9/1045; G16H 40/20

USPC ................................ 340/286.07, 506, 573.1
See application file for complete search history.

(56) References Cited

U.S. PATENT DOCUMENTS

| 4,130,737 A * | 12/1978 | Breen ................... H04M 9/002 379/158 |
| 6,094,585 A * | 7/2000 | Dajer .................. H04W 52/343 370/335 |
| 2017/0221344 A1* | 8/2017 | Cox ........................ G16H 40/67 |
| 2018/0106897 A1* | 4/2018 | Shouldice ............ A61B 5/7264 |

* cited by examiner

*Primary Examiner* — Daryl C Pope
(74) *Attorney, Agent, or Firm* — Hodgson Russ LLP

(57) ABSTRACT

The present disclosure may be embodied as a pillow speaker system. The pillow speaker system includes a nurse call patient station and a patient interface device (PID). The PID is in electronic communication with the nurse call patient station, and includes a wired communication link connected to the nurse call patient station and an energy storage device for providing backup power to the PID. The energy storage device is galvanically isolated from the wired communication link. The PID is configured to receive audio signals from the nurse call patient station by way of the wired communication link. The PID may also include a power port for receiving electrical power from an external source. The power port is galvanically isolated from the wired communication link.

41 Claims, 5 Drawing Sheets

NURSE CALL PILLOW SPEAKER WITH BROWNOUT PROTECTION

FIELD OF THE DISCLOSURE

The present disclosure is generally directed to an electronic device that is used in a health care setting, such as a hospital, nursing home, clinic, or similar environment. By way of example, the electronic device may be a hand-held pillow speaker kept at a patient's bedside for remotely controlling a television, room lights, or other electronic items in the room, and for communicating with nursing staff or other personnel.

BACKGROUND OF THE DISCLOSURE

Traditional hospital pillow speakers and handheld pendants do not typically receive power independent from the nurse call system to which they are connected. A typical arrangement is illustrated in FIG. 1. The limited power supply capabilities of the nurse call system may restrict the capabilities and features of such devices. In other cases, pillow speakers and pendants may be passive devices which do not consume power at all, and may merely provide passive contact closure switches for signaling to the nurse call master station. Pillow speakers that draw power from the nurse call system are subject to the same power interruptions experienced by the nurse call system.

Interruptions in the electrical power supplied to hospitals, whether to the primary power system or any number of subsystems, may occur frequently due to the requirements for hospitals to test emergency power supply systems. Such interruptions are termed "brownouts." Brownouts may occur for very short periods as the emergency system switches from a normal power source to an alternate power source, or for longer periods of time depending on the condition and performance of the emergency system or the type of test. Further, certain electrical branches may be deemed nonessential and will not switch over to an alternative power source in the absence of a primary source. Brownouts may also occur outside of planned hospital tests due to weather or other natural events disrupting the electrical grid supplying the hospital, or due to unplanned mechanical or electrical equipment failures.

As pillow speakers grow in capability and offer more features, such as tablets or other patient interaction devices (PIDs), the power demands of the pillow speakers also increase. Electrical power may be supplied to a pillow speaker from a secondary source separate from the power supplied from the nurse call patient station, such as a branched circuit connected to a wall outlet. As such PIDs are dependent on secondary power, they may not have the benefit of the nurse call system for protection from power interruption. As such, there is a critical, long-felt need for a nurse call pillow speaker with improved resistance to brownouts.

BRIEF SUMMARY OF THE DISCLOSURE

In an aspect of the present disclosure, a pillow speaker system is presented. The pillow speaker system includes a nurse call patient station and a patient interface device (PID). The PID is in electronic communication with the nurse call patient station, and includes a wired communication link connected to the nurse call patient station and an energy storage device for providing backup power to the PID. The energy storage device is galvanically isolated from the wired communication link, as it has no direct current path to the wired communication link. The PID is configured to receive electronic signals from the nurse call patient station by way of the wired communication link. The PID may also include a power port for receiving electrical power from an external source. The power port is galvanically isolated from the wired communication link. The energy storage device may include an electrochemical device. The energy storage device may be a battery and/or a supercapacitor. The energy storage device may be rechargeable. The PID may further include an audio speaker. The PID may be a pillow speaker.

The PID may further include a detection circuit configured to detect an interruption in electrical power received by way of the power port. The PID may further include a switching circuit configured to supply the PID with the backup power when the detection circuit detects an interruption.

In another aspect of the present disclosure, a pillow speaker system is presented. The pillow speaker system includes a patient hub and a PID in electronic communication with the patient hub. The patient hub includes a communication port configured to be connected to a nurse call patient station, a first power port for receiving electrical power from an external source, and a first energy storage device for providing backup power to the patient hub. The first power port is galvanically isolated from the communication port. The PID includes a wired communication link connected to the patient hub and a second energy storage device for providing backup power to the PID. The PID is configured to receive electronic signals received from the nurse call patient station by way of the wired communication link. The communication port may be configured to transmit and receive analog signals. The patient hub may be configured to condition the analog signals. The communication port may be configured to transmit and receive digital signals. The patient hub may be configured to encode the digital signals with a codec. The PID may further include an audio speaker. The audio speaker may be bidirectional.

The first and second energy storage devices may include an electrochemical device. The first and second energy storage devices may be batteries and/or supercapacitors. The first and second energy storage devices may be rechargeable.

The patient hub may further include a detection circuit configured to detect an interruption in electrical power received by way of the first power port. The patient hub may further comprise a switching circuit configured to supply the PID with the backup power from the first energy storage device when the detection circuit detects an interruption. The PID may further comprise a switching circuit configured to supply the PID with the backup power from the second energy storage device when the detection circuit detects an interruption.

The PID may be a pillow speaker. The pillow speaker may include an audio input, such as a microphone. The wired communication link may be configured to convey patient audio from the microphone to the nurse call patient station. The pillow speaker may further include a display screen. The display screen may be a touchscreen.

In another aspect of the present disclosure, a pillow speaker is presented. The pillow speaker includes a communication line configured to be connected to a nurse call patient station and an energy storage device for providing backup electrical power to the pillow speaker. The pillow speaker is configured to receive electronic signals received from the nurse call patient station by way of the communication line. The energy storage device is device is galvanically isolated from the communication line, as it has no direct current path to the communication line. The pillow speaker may further include a power port for receiving electrical power from an external source. The power port is galvanically isolated from the communication link. The energy storage device may include an electrochemical device. The energy storage device may be a battery and/or a supercapacitor. The energy storage device may be rechargeable. The pillow speaker may include an audio speaker.

The pillow speaker may further include a detection circuit configured to detect an interruption in electrical power received by way of the communication line. The pillow speaker may further include a switching circuit configured to supply the pillow speaker with the backup power when the detection circuit detects an interruption in electrical power received by way of the communication line. The pillow speaker may further include a detection circuit configured to detect an interruption in electrical power received by way of the power port. The pillow speaker may further include a switching circuit configured to supply the pillow speaker with the backup power when the detection circuit detects an interruption in electrical power received by way of the power port.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Figure 1:
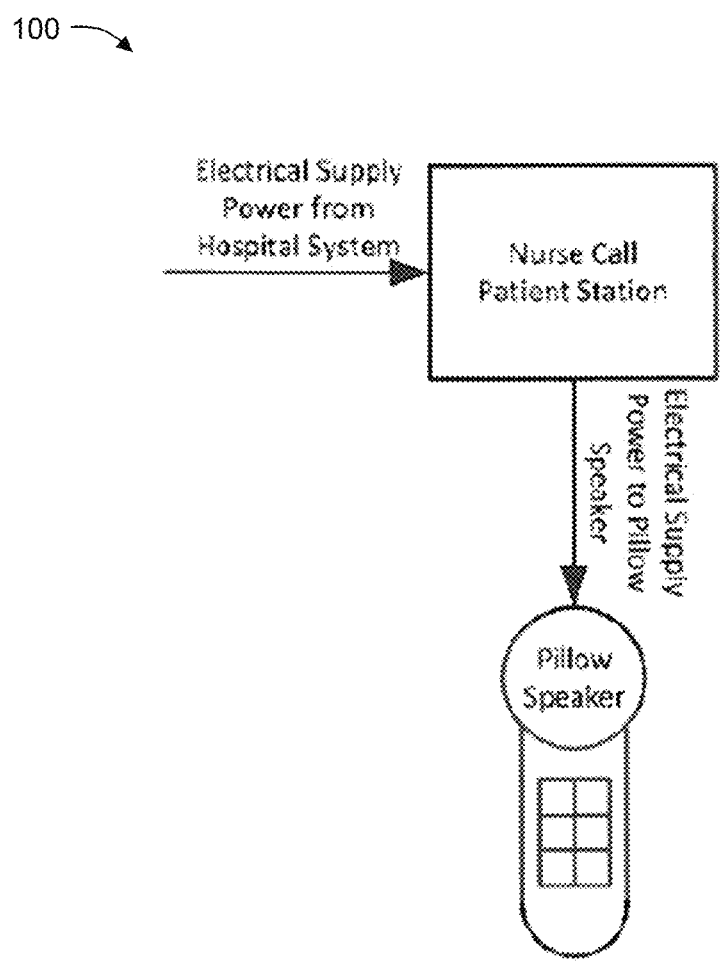
FIG. 1 is a block diagram of a prior art pillow speaker system.
Figure 2:
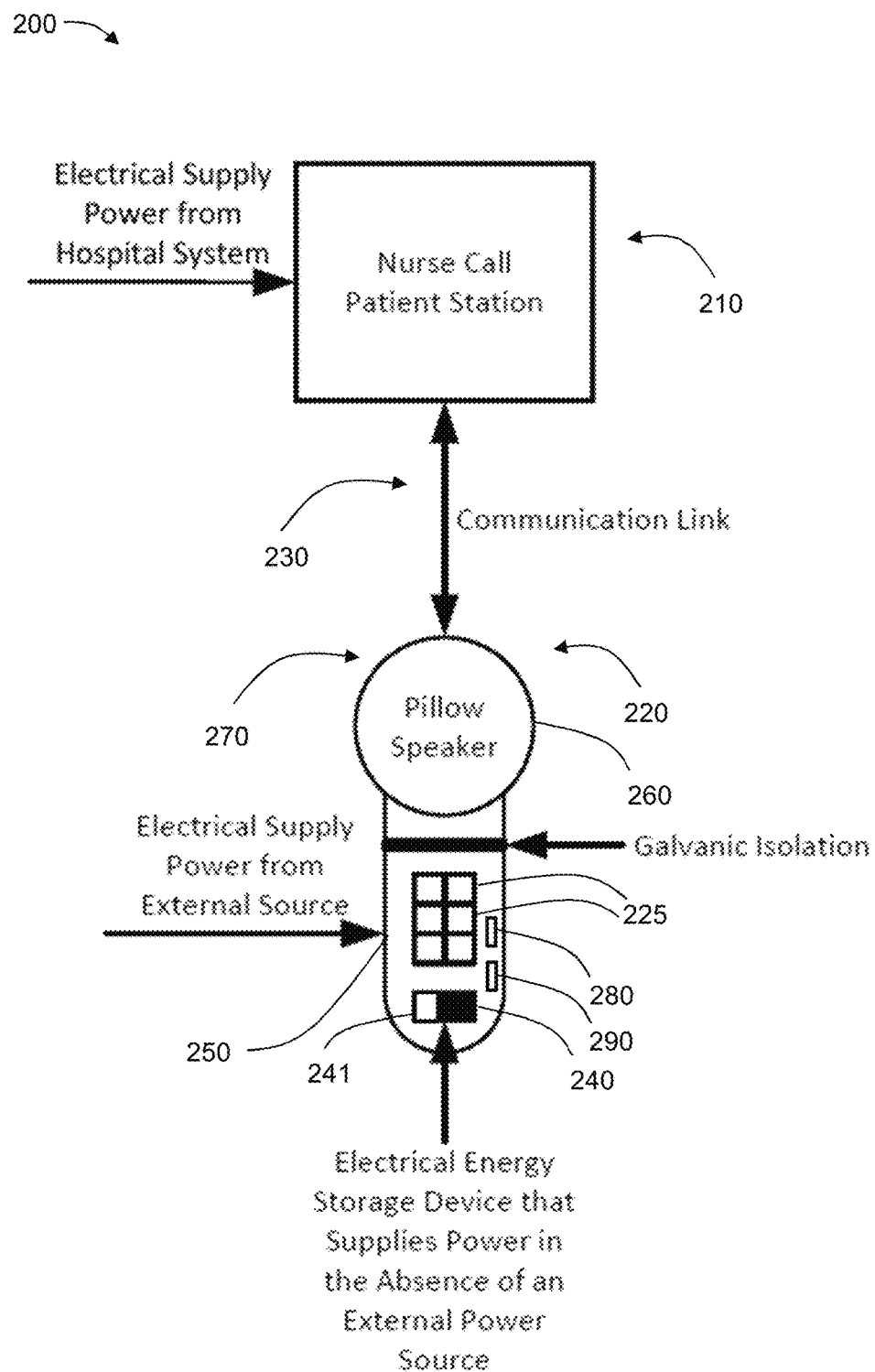
FIG. 2 is a block diagram of a first embodiment of a pillow speaker system with brownout protection according to the present disclosure.

In an aspect of the present disclosure, and with reference to FIG. 2, a pillow speaker system 200 is presented. The pillow speaker system 200 includes a nurse call patient station 210 and a patient interface device (PID) 220. The nurse call patient station 210 is typically located inside a hospital room, and facilitates communication between a patient inside the room and an external monitoring station outside of the room. The PID 220 may be any device which allows the patient to communicate with the nurse call patient station. The PID 220 may include an audio speaker 260. The audio speaker may output sound originating from the external monitoring station (such the voice of a caregiver), audio originating from an entertainment system (such as a television set), or audio originating from the PID 220 itself (such as a PID 220 configuration including a built-in tablet computer). The PID 220 may include a microphone for audio input. The PID 220 may be a pillow speaker 270. The PID 220 may be a tablet computer. The PID 220 may be a handheld pendant. The PID 220 may have one or more physical buttons 225 for patient input. The PID 220 may have a touchscreen. The PID 220 may provide tactile feedback to the patient via the buttons or the touchscreen. The PID 220 may be configured to control the entertainment system or other aspects of the hospital room, such as lights or window blinds. The PID 220 may be Wi-Fi and/or Bluetooth-enabled for connection to the Internet, hospital intranet, and/or other in-room devices.

The PID 220 is in electronic communication with the nurse call patient station 210, and includes a wired communication link 230 connected to the nurse call patient station 210 and an energy storage device 240 for providing backup power to the PID 220. The energy storage device 240 is galvanically isolated from the wired communication link 230. In galvanic isolation, two functional sections of an electronic system have no conductive path between them to prevent direct current flow. Energy or information may still be exchanged between the sections by other means, such as through capacitive coupling, electromagnetic induction, magnetic sensing, or by optical, acoustic, or mechanical means. Galvanic isolation of two functional sections may be achieved using one or more transformers coupled by magnetic flux, opto-isolators transmitting information in light waves, capacitors allowing alternating current (AC) to flow, Hall effect sensors that convert information from a magnetic field to a voltage, or magnetocouplers that store information as a magnetic field.

The PID 220 is configured to receive electronic signals from the nurse call patient station 210 by way of the wired communication link 230. The electronic signals may be analog data and/or audio signals, wherein the analog data signals are normally open or closed dry contacts that connect or disconnect a circuit, voltage levels derived from a resistor network, or voltages and currents sufficient to illuminate on or more light emitting diodes (LEDs). The electronic signals may be digital data signals, including audio signals encoded as digital data signals. The wired communication link 230 may be a Universal Serial Bus (USB) connection or other suitable connection. The PID 220 may also include a power port 250 for receiving electrical power from an external source. The power port 250 is galvanically isolated from the wired communication link 230. The energy storage device 240 may include an electrochemical device 241. The energy storage device 240 may be a battery and/or a supercapacitor. The energy storage device 240 may be rechargeable.

The PID 220 may further include a detection circuit 280 configured to detect an interruption in electrical power received by way of the power port 250. When the detection circuit 280 detects an interruption, the detection circuit 280 may configure the PID 220 to source power from the energy storage device 240. For example, the detection circuit 280 may be a voltage comparator that monitors voltages from the power port 250 and the energy storage device 240, such that the power port voltage, when present, is greater than the energy storage device voltage, and the power port voltage, where not present, is less than the energy storage device voltage. Alternatively, the PID 220 may further include a switching circuit 290 configured to supply the PID with the backup power when the detection circuit 280 detects an interruption. Once electrical power from the power port 250 is restored, the detection circuit 280 may reconfigure the PID 220 to source power from the power port 250 as initially arranged. For example, when the voltage comparator detects that a power port voltage is present, it may turn on a transistor to connect the PID 220 to the power port 250 and turn off a transistor to disconnect the PID 220 from the energy storage device 240. Further, when the voltage comparator detects power port voltage is interrupted, the voltage comparator may turn on a transistor to connect the PID 220 to the energy storage device 240 and turn off the transistor to disconnect the PID 220 from the power port 250. Alternatively, once electrical power from the power port 250 is restored, the switching circuit 290 may be reconfigured to source power from the power port 250 to the PID 220 as initially arranged. In cases where the response times of the detection 280 and switching circuits 290 are slower than the interruption of electrical power received by way of the power port 250, additional bulk bypass capacitors may be used to supply power while the detection 280 and switching circuits 290 connect the energy storage device 240. From the patient's perspective, the transition between power sources occurs nearly instantaneously and transparently. As a result, the patient experiences no loss in capability or functionality during a brownout. Further, when the brownout ends, there is no need to reboot the PID 220 and interrupt operation, as the PID 220 remains ready for communication when its primary power is restored as if no brownout had occurred.

Figure 3:
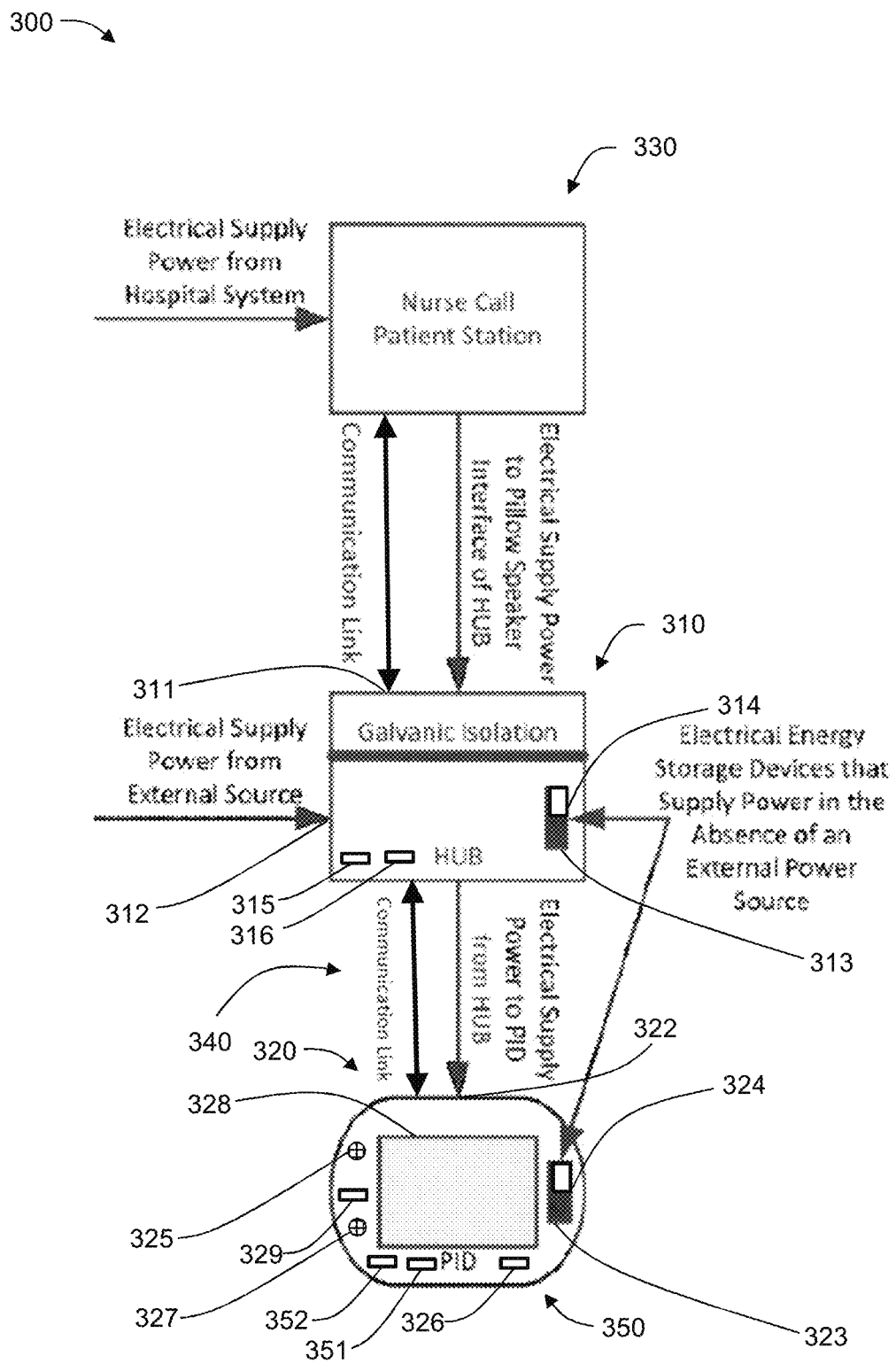
FIG. 3 is a block diagram of a second embodiment of a pillow speaker system with brownout protection according to the present disclosure.
Figure 4:
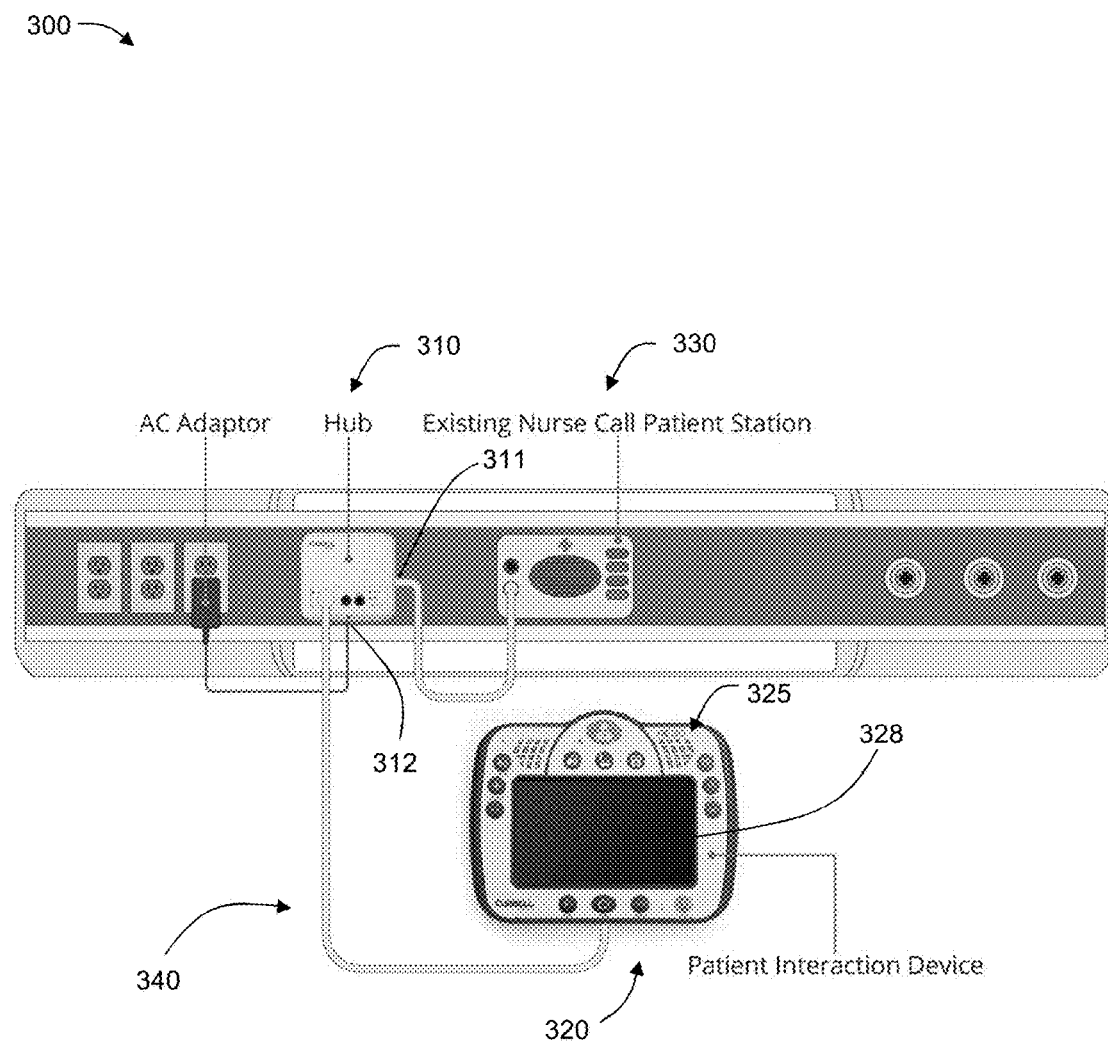
FIG. 4 is a two dimensional rendering of the second embodiment of the pillow speaker system with brownout protection according to the present disclosure.

In another aspect of the present disclosure, and with reference to FIGS. 3 and 4, a pillow speaker system 300 is presented. The pillow speaker system 300 includes a patient hub 310 and a PID 320 in electronic communication with the patient hub 310. The patient hub 310 is a device configured to supply the PID 320 with a consistent level of power. The patient hub 310 may also be configured to manage data priorities to nurse call and hospital systems via a wired communication link. The patient hub 310 may also support other electronic communication methodologies, such Ethernet, Wi-Fi, and Bluetooth connections. The patient hub 310 may also include back-mounted, hard-wired connections to television and room auxiliary terminals. The patient hub 310 is the data distribution terminal for the PID 320, the nurse call system connection, and the primary system power supply. The patient hub 310 may be powered by an AC adapter plugged into a wall outlet. The patient hub 310 may further include additional inputs (such as ¼" input jacks) for optional accessories, such as specialty call cords and fall management devices.

The patient hub 310 includes a communication port 311 configured to be connected to a nurse call patient station 330, a first power port 312 for receiving electrical power from an external source, and a first energy storage device 313 for providing backup power to the patient hub. The first power port 312 is galvanically isolated from the communication port 311. The PID 320 includes a wired communication link 340 connected to the patient hub 310 and a second energy storage device 323 for providing backup power to the PID 320. The PID 320 is configured to receive electronic signals from the nurse call patient station 330 by way of the wired communication link 340. The electronic signals may be analog data and/or audio signals, wherein the analog data signals are normally open or closed dry contacts that connect or disconnect a circuit, voltage levels derived from a resistor network, or voltages and currents sufficient to illuminate on or more light emitting diodes (LEDs). The electronic signals may be digital data signals, including audio signals encoded as digital data signals. The wired communication link 340 may be a USB connection or other suitable connection. The communication port 311 may be configured to transmit and receive analog signals. The patient hub 310 may be configured to condition the analog signals. For example, the patient hub 310 may be configured to increase the voltage amplitude and/or current magnitude of the analog signals using an operational amplifier so that a load may be driven.

In another example, the patient hub 310 may be configured to pass the analog signals through a passive first-order or active second-order low-pass filter to attenuate out-of-band and unwanted noise. In a further example, the patient hub 310 may be configured to galvanically isolate the analog signals so that there is no electrically conductive direct current path between the source and the termination of the analog signals. The communication port 311 may be configured to transmit and receive digital signals that may employ an established serial or parallel communication protocol and physical signaling layer. The patient hub 310 may be configured to encode the analog signals to digital signals and/or decode the digital signals to analog signals with a codec. The PID 320 may further include an audio speaker 325. The audio speaker 325 may be bidirectional.

The first and second energy storage devices 313,323 may include an electrochemical device 314,324. The first and second energy storage devices 313,323 may be batteries and/or supercapacitors. The first and second energy storage devices 313,323 may be rechargeable.

The patient hub 310 may further include a detection circuit 315 configured to detect an interruption in electrical power received by way of the first power port 312. When the detection circuit 315 detects an interruption, the detection circuit 315 may configure the patient hub 310 to source power from the first energy storage device 313. Alternatively, the patient hub 310 may further comprise a switching circuit 316 configured to supply the patient hub 310 with the backup power from the first energy storage device 313 when the detection circuit 315 detects an interruption.

Further, when the detection circuit 315 detects an interruption, the detection circuit 315 may configure the PID 320 to source power from the second energy storage device 323. Alternatively, the PID 320 may further comprise a switching circuit 326 configured to supply the PID 320 with the backup power from the second energy storage device 323 when the detection circuit 315 detects an interruption. Once electrical power from first power port 312 is restored, the detection circuit 315 may reconfigure the patient hub 310 to source power from the first power port 312, and may also reconfigure the PID 320 to source power from the patient hub 310, as initially arranged. Alternatively, the switching circuit 316 may be reconfigured to source power from the first power port 312 to the patient hub 310, and may also be reconfigured to source power from the patient hub 310 to the PID 320 as initially arranged.

In another embodiment of the present invention, the PID 320 may further include a detection circuit 329 configured to detect an interruption in electrical power received by way of the second power port 322. The PID may further include a switching circuit 326 configured to supply the PID with the backup power from the second energy storage device 323 when the detection circuit 329 detects an interruption. Once electrical power from second power port 322 is restored, the detection circuit 329 may reconfigure the PID 320 to source power from the second power port 322, as initially arranged. Alternatively, the switching circuit 326 may be reconfigured to source power from the second power port 322 to the PID 320 as initially arranged.

The PID 320 may be a pillow speaker 350. The pillow speaker may include an audio input 327, such as a microphone. The wired communication link 340 may be configured to convey patient audio from the microphone to the nurse call patient station. The pillow speaker 350 may further include a display screen 328. The display screen 328 may be a touchscreen. The PID 320 may include a processor 351 and a non-transitory computer-readable medium 352.

Sources of patient entertainment, such as audio or video files, may be stored on the non-transitory computer-readable medium 352 of the PID 320. Other sources of patient entertainment may be stored externally to the PID 320 and displayed via the display screen 328 of the PID 320. The PID 320 may be sized similar to a tablet or large smartphone.

Figure 5:
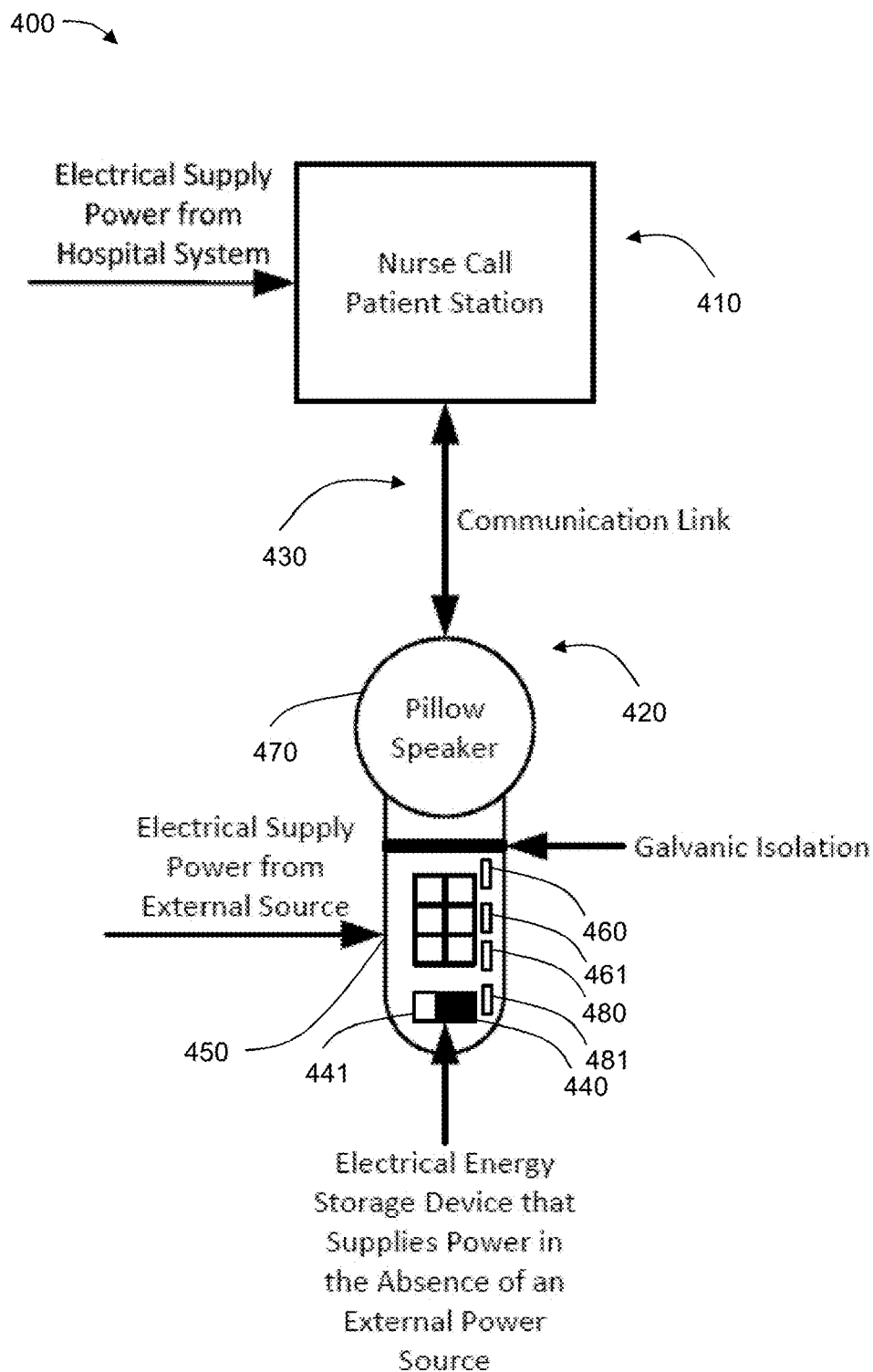
FIG. 5 is a block diagram of a third embodiment of a pillow speaker with brownout protection according to the present disclosure.

In another aspect of the present disclosure, and with reference to FIG. 5, a pillow speaker 420 is presented. The pillow speaker includes a communication line 430 configured to be connected to a nurse call patient station 410 and an energy storage device 440 for providing backup electrical power to the pillow speaker 420. The pillow speaker 420 is configured to receive electronic signals from the nurse call patient station 410 by way of the communication line 430. The electronic signals may be analog data and/or audio signals, wherein the analog data signals are normally open or closed dry contacts that connect or disconnect a circuit, voltage levels derived from a resistor network, or voltages and currents sufficient to illuminate on or more light emitting diodes (LEDs). The electronic signals may be digital data signals, including audio signals encoded as digital data signals. The energy storage device 440 is galvanically isolated from the communication line 430. The pillow speaker 420 may further include a power port 450 for receiving electrical power from an external source. The power port 450 is galvanically isolated from the communication link 430. The energy storage device 440 may include an electrochemical device 441. The energy storage device 440 may be a battery and/or a supercapacitor. The energy storage device 440 may be rechargeable. The pillow speaker 420 may include an audio speaker 470.

The pillow speaker 420 may further include a detection circuit 460 configured to detect an interruption in electrical power received by way of the communication line 430. When the detection circuit 460 detects an interruption, the detection circuit 460 may configure the pillow speaker 420 to source power from the energy storage device 440. Alternatively, the pillow speaker 420 may further include a switching circuit 461 configured to supply the pillow speaker 420 with backup power when the detection circuit 460 detects an interruption in electrical power received by way of the communication line 430. Once electrical power from the communication line 430 is restored, the detection circuit 460 reconfigures the pillow speaker 420 to source power from the communication line 430 as initially arranged. Alternatively, the switching circuit 461 may reconfigure the pillow speaker 420 to source power from the communication line 430 as initially arranged.

The pillow speaker 420 may further include a detection circuit 480 configured to detect an interruption in electrical power received by way of the power port 450. When the detection circuit 480 detects an interruption, the detection circuit 480 may configure the pillow speaker 420 to source power from the energy storage device 440. Alternatively, the pillow speaker 420 may further include a switching circuit 481 configured to supply the pillow speaker 420 with the backup power when the detection circuit 480 detects an interruption in electrical power received by way of the power port 450. Once electrical power from the power port 450 is restored, the detection circuit 480 reconfigures the pillow speaker 420 to source power from the power port 450 as initially arranged. Alternatively, the switching circuit 481 may reconfigure the pillow speaker 420 to source power from the power port 450 as initially arranged.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

I claim:

1. A pillow speaker system, comprising:
a nurse call patient station; and
a patient interface device (PID) in electronic communication with the nurse call patient station, comprising:
 a wired communication link connected to the nurse call patient station;
 an energy storage device for providing backup power to the PID;
 wherein the PID is configured to receive electronic signals from the nurse call patient station by way of the wired communication link; and
 wherein the energy storage device is galvanically isolated from the wired communication link.

2. The system of claim 1, wherein the electronic signals are analog signals.

3. The system of claim 1, wherein the electronic signals are digital signals.

4. The system of claim 1, wherein the PID further comprises a power port for receiving electrical power from an external source, wherein the power port is galvanically isolated from the wired communication link.

5. The system of claim 4, wherein the PID further comprises a detection circuit configured to detect an interruption in electrical power received by way of the power port.

6. The system of claim 5, wherein the PID further comprises a switching circuit configured to supply the PID with the backup power when the detection circuit detects an interruption.

7. The system of claim 1, wherein the PID further comprises an audio speaker.

8. The system of claim 1, wherein the energy storage device comprises an electrochemical device.

9. The system of claim 1, wherein the energy storage device is a battery and/or a supercapacitor.

10. The system of claim 1, wherein the PID is a pillow speaker.

11. A pillow speaker system, comprising:
a patient hub, comprising:
 a communication port configured to be connected to a nurse call patient station;
 a first power port for receiving electrical power from an external source, wherein the power port is galvanically isolated from the communication port; and
 a first energy storage device for providing backup power to the patient hub; and
a patient interface device (PID) in electronic communication with the patient hub, the PID comprising:
 a wired communication link connected to the patient hub;
 a second energy storage device for providing backup power to the PID;
 a second power port for receiving electrical power from the patient hub; and
 wherein the PID is configured to receive electronic signals received from the nurse call patient station by way of the wired communication link.

12. The system of claim 11, wherein the electronic signals are analog signals.

13. The system of claim 11, wherein the electronic signals are digital signals.

14. The system of claim 11, wherein the patient hub further comprises a detection circuit configured to detect an interruption in electrical power received by way of the first power port.

15. The system of claim 14, wherein the patient hub further comprises a switching circuit configured to supply the PID with the backup power from the first energy storage device when the detection circuit detects an interruption.

16. The system of claim 14, wherein the PID further comprises a switching circuit configured to supply the PID with the backup power from the second energy storage device when the detection circuit detects an interruption.

17. The system of claim 11, wherein the PID further comprises a detection circuit configured to detect an interruption in electrical power received by way of the second power port.

18. The system of claim 17, wherein the PID further comprises a switching circuit configured to supply the PID with the backup power from the second energy storage device when the detection circuit detects an interruption.

19. The system of claim 11, wherein the PID further comprises an audio speaker.

20. The system of claim 19, wherein the audio speaker is bidirectional.

21. The system of claim 11, wherein the PID is a pillow speaker.

22. The system of claim 11, wherein the PID further comprises an audio input.

23. The system of claim 11, wherein the first and second energy storage devices each comprise an electrochemical device.

24. The system of claim 11, wherein the first and second energy storage devices are batteries and/or supercapacitors.

25. The system of claim 11, wherein the communication port is configured to transmit and receive analog signals.

26. The system of claim 25, wherein the patient hub is configured to condition the electronic signals.

27. The system of claim 11, wherein the communication port is configured to transmit and receive digital signals.

28. The system of claim 27, wherein the patient hub is configured to encode and/or decode the digital signals with a codec.

29. The pillow speaker system of claim 11, wherein the PID further comprises a display screen.

30. The pillow speaker system of claim 29, wherein the display screen is a touchscreen.

31. A pillow speaker, comprising:
a communication line configured to be connected to a nurse call patient station;
an energy storage device for providing backup electrical power to the pillow speaker;
wherein the pillow speaker is configured to receive electronic signals from the nurse call patient station by way of the communication line; and
wherein the energy storage device is galvanically isolated from the communication line.

32. The system of claim 31, wherein the electronic signals are analog signals.

33. The system of claim 31, wherein the electronic signals are digital signals.

34. The pillow speaker of claim 31, wherein the pillow speaker further comprises a power port for receiving electrical power from an external source, wherein the power port is galvanically isolated from the communication link.

35. The pillow speaker of claim 31, wherein the pillow speaker further comprises a detection circuit configured to detect an interruption in electrical power received by way of the communication line.

36. The pillow speaker of claim 35, wherein the pillow speaker further comprises a switching circuit configured to supply the pillow speaker with the backup power when the detection circuit detects an interruption in electrical power received by way of the communication line.

37. The pillow speaker of claim 31, wherein the pillow speaker further comprises a detection circuit configured to detect an interruption in electrical power received by way of the power port.

38. The pillow speaker of claim 37, wherein the pillow speaker further comprises a switching circuit configured to supply the pillow speaker with the backup power when the detection circuit detects an interruption in electrical power received by way of the power port.

39. The pillow speaker of claim 30, wherein the pillow speaker comprises an audio speaker.

40. The pillow speaker of claim 31, wherein the energy storage device comprises an electrochemical energy storage device.

41. The pillow speaker of claim 31, wherein the energy storage device is a battery and/or a supercapacitor.

* * * * *